(12) United States Patent
Itzhak et al.

(10) Patent No.: US 8,603,391 B2
(45) Date of Patent: Dec. 10, 2013

(54) APPARATUS AND METHOD FOR AIR TREATMENT AND SANITIZATION

(75) Inventors: David Itzhak, Tel-Aviv (IL); Michael Dov Teicher, Reut (IL)

(73) Assignee: Megair Ltd., Rishon-Le-Zion (IL)

( * ) Notice: Subject to any disclaimer, the term of this patent is extended or adjusted under 35 U.S.C. 154(b) by 0 days.

(21) Appl. No.: 12/735,924

(22) PCT Filed: Mar. 1, 2009

(86) PCT No.: PCT/IL2009/000227
§ 371 (c)(1),
(2), (4) Date: Nov. 24, 2010

(87) PCT Pub. No.: WO2009/107138
PCT Pub. Date: Sep. 3, 2009

(65) Prior Publication Data
US 2011/0110816 A1    May 12, 2011

(51) Int. Cl.
*A61L 9/00* (2006.01)
(52) U.S. Cl.
USPC ................................. 422/4; 422/121; 422/37
(58) Field of Classification Search
USPC .......................................... 422/4, 28, 38, 121
See application file for complete search history.

(56) References Cited

U.S. PATENT DOCUMENTS

| | | | |
|---|---|---|---|
| 4,343,765 A | 8/1982 | Elston | |
| 4,685,617 A | 8/1987 | Assaf | |
| 4,872,315 A | 10/1989 | Assaf | |
| 5,009,869 A | 4/1991 | Weinberg | |
| 5,688,385 A | 11/1997 | Rhees | |
| 5,792,369 A | 8/1998 | Johnson | |
| 5,902,619 A | 5/1999 | Rubow | |
| 2002/0056285 A1 | 5/2002 | Elich | |
| 2002/0098128 A1 | 7/2002 | Smith | |
| 2003/0164309 A1 | 9/2003 | Nakamura | |
| 2004/0231512 A1 | 11/2004 | Slayzak | |
| 2004/0261952 A1 | 12/2004 | Hart | |
| 2007/0148256 A1 | 6/2007 | Yanagihara | |
| 2010/0043632 A1 | 2/2010 | Itzhak | |

FOREIGN PATENT DOCUMENTS

| | | |
|---|---|---|
| EP | 0 230 875 | 8/1987 |
| JP | 2004-089770 | 3/2004 |
| WO | 94/11091 | 5/1994 |
| WO | 01/78868 | 10/2001 |
| WO | 2004/027116 | 4/2004 |
| WO | 2007/026363 | 3/2007 |

OTHER PUBLICATIONS

International Search Report for PCT/IL2009/000227, mailed Jul. 8, 2009.
Written Opinion for PCT/IL2009/000227, mailed Jul. 8, 2009.
Ovreas et al., Characterization of Microbial Diversity in Hypersaline Environments by Melting Profiles and Reassociation Kinetics in Combination with Terminal Restriction Fragment Length Polymorphism (T-RFLP), Microbiology Ecology, (2003), vol. 46, pp. 291-301.

*Primary Examiner* — Sean E Conley
(74) *Attorney, Agent, or Firm* — Nixon & Vanderhye P.C.

(57) ABSTRACT

A method for reducing the biological contamination of indoor air and sanitizing the walls and surfaces in a closed space, which method comprises causing a stream of air to flow upwardly through a treatment zone, and to contact, on a substantially horizontally aligned perforated surface, with a stream of brine solution having Redox potential of not less than 500 mV, whereby an active layer is formed on said horizontally aligned perforated surface, in which layer the brine and air mix, and delivering the treated air which exits said treatment zone into the space to be sanitized.

7 Claims, 4 Drawing Sheets

Fig. 4A Control

Fig. 4B

Fig. 4C Control

APPARATUS AND METHOD FOR AIR TREATMENT AND SANITIZATION

This application is the U.S. national phase of International Application No. PCT/IL2009/000227 filed 1 Mar. 2009, which designated the U.S. and claims priority to U.S. Application Nos. 61/064,326, filed 28 Feb. 2008 and 61/064,327, filed 28 Feb. 2008, the entire contents of each of which are hereby incorporated by reference.

Commonly used methods for treating contaminated air are based on filtration, air ionization and sterilization of air by means of ozone or ultraviolet light.

WO 2007/026363 describes a method for reducing the level of microorganism of indoor air, by contacting a stream of indoor air with a concentrated salt solution, which is preferably halide brine having a Redox (reduction-oxidation) potential in the range between 200 mV and 450 mV. The publication identifies certain brines that are capable of developing such Redox potentials under suitable aeration conditions, and alternatively or in addition, proposes to electrolyze the brine in an electrolytic cell, whereby the Redox potential of the brine is suitably adjusted. WO 2007/026363 also specifically describes a packed column scrubber (in which the air and the brine solution are brought into contact via solid material filling the column) for running the method set forth above in various facilities, including hospitals.

It has been demonstrated that operating under the preferred treatment regime according to WO 2007/026363, using brines having Redox potentials in the range between 200 and about 450 mV, effectively reduces the level of biological contaminants of indoor air. There exists a need, however, in certain facilities, to periodically sanitize the walls and other surfaces in closed spaces.

It has now been found that the sanitization of a closed space is feasible by causing the air in said space to flow upwardly through a column, and to contact, on a substantially horizontally aligned perforated surface, with a downwardly flowing stream of brine solution whose Redox potential exceeds 500 mV, whereby an active layer is formed on said perforated surface, in which the brine and air mix together. As used herein, the term "sanitization" indicates a treatment exhibiting a bactericidal or fungicidal effect. It is believed that various oxidant species, such as halogens, oxycompounds of halogens, oxygen or radicals thereof produced in an electrolyzed brine solution, are released into the air contacting the brine in the active layer. The aforementioned chemical species are carried by the treated air stream onto the walls and other surfaces in the closed space (e.g., of equipment and goods placed in said closed space), thus achieving a reduction of the biological contamination and accomplishing the sanitization of said walls and surfaces.

Accordingly, the invention provides a method for reducing the biological contamination of indoor air and sanitizing the walls and surfaces in a closed space, which method comprises causing a stream of air to flow upwardly through a treatment zone, and to contact, on a substantially horizontally aligned perforated surface placed within said treatment zone, with a stream of brine solution having Redox potential of not less than 500 mV, whereby an active layer is formed on said perforated surface, in which layer the brine and air mix, and delivering the treated air which exits said treatment zone into the space to be sanitized. The treatment zone is most suitably provided by a vertically positioned column, in which the stream of brine solution flows downwardly.

The term "treated air" indicates the air which passed through the active layer. The term "brine solution", as used herein, refers to dilute, concentrated, nearly saturated or saturated salt solutions, namely, solutions wherein the concentration of the salt dissolved therein is not less than 0.1% (w/w), preferably not less than 1.0%, more preferably not less than 10% or 20% (w/w), and up to saturation at the relevant temperature. Compositionally, the concentrated salt solution operative in the present invention may be an aqueous solution containing one or more water soluble salts represented by the formulas MX, $M_2X$ and $MX_2$, wherein X is selected from the group consisting of chloride, bromide, iodide, sulfate and nitrate anions, and M indicates a metal cation, which is most preferably selected from the group consisting of lithium, sodium, potassium, calcium, magnesium and zinc, and mixtures thereof. Preferred brine solutions include concentrated solutions of sodium chloride or calcium chloride (with a concentration of not less than 10 wt %, and preferably not less than 20 wt %). Another preferred concentrated salt solution to be used according to the invention comprises a mixture of at least one bromide or iodide salt, in combination with at least one chloride salt of one or more of the following metals: $Na^+$, $K^+$, $Mg^{2+}$ and $Ca^{2+}$. Another possible solution contains a mixture of bromide and chloride salts dissolved therein in a total concentration of 30 to 40% by weight, with the cationic species being $Mg^{2+}$, $Ca^{2+}$, $Na^+$ and $K^+$. More specifically, the concentrations of the aforementioned ions are as follows: $Mg^{2+}$: 30-50 g/liter; $Ca^{2+}$: 10-20 g/liter; $Na^+$: 30-50 g/liter; $K^+$: 5-10 g/liter; $Cl^-$: 150-240 g/liter; $Br^-$: 3-10 g/liter. An example of such a solution is provided by the Dead Sea brine, which has the following typical (average) mineral composition: $Mg^{2+}$: about 40.6 g/liter; $Ca^{2+}$: about 16.8 g/liter; $Na^+$: about 39.1 g/liter; $K^+$: about 7.26 g/liter; $Cl^-$: about 212.4 g/liter; $Br^-$: about 5.12 g/liter, with the total concentration of salts dissolved therein being 33% by weight. Another possible concentrated salt solution comprises a mixture of bromide and chloride salts dissolved in water in a total concentration of 30 to 40% by weight, with the cationic species being $Mg^{2+}$, $Ca^{2+}$, $Na^+$ and $K^+$, wherein the concentration of calcium chloride in said solution is effective in reducing the rate of evaporation of water therefrom, and is preferably in the range between 20 and 200 g/liter.

The Redox potentials reported herein are measured using Pt/Ag/AgCl electrodes, thus indicating the electrochemical potential which is developed between Pt electrode exposed to the brine solution and a standard silver-silver chloride electrode.

The brine solution circulates through the treatment zone. The treatment zone, namely, the column, is divided by the horizontally aligned, perforated, contacting surface into lower and upper sections. The brine solution is fed to the column in the upper section, flows downwardly through the column, and is collected in the lower section of the column below the perforated surface. In order to increase the Redox potential of the brine solution, namely, to generate a brine solution having a Redox potential above 500 mV, and specifically between 500-1000, the brine is electrolyzed in an electrolytic cell. The term "electrolytic cell", as used herein, refers specifically to a set-up comprising electrodes connected to the opposite poles of a direct electrical current (DC) power supply. The electrolytic cell is placed in any suitable location in the pathway of the circulating brine. In its most simple configuration, an electrolytic cell suitable for use according to the present invention comprises two electrodes that are affixed within a reservoir used for holding the brine, or alternatively, within a feed line used to transfer the brine from its reservoir to the upper section of the column, above the horizontally aligned perforated surface. The electrodes are preferably placed in parallel to each other, separated by a gap of 0.3 to 2.0 cm, and more preferably of 0.5 to 1.0 cm. The electrodes are preferably in the form of plates or meshes having a length and a width of about 2 and 10 cm, respectively. The electrodes are generally composed of a metal selected from the group consisting of Ti, Nb and Ta, coated with Pt, Ru, RuO2 and Ir. Platinum, an alloy of platinum and iridium and electrodes of the type M-MO (wherein M designates a metal, and MO a metal oxide, such as Ir—TaO2) may also be used. The cell typically operates at a current density of $10^3$-$10^5$ Ampere per square meter of anode, applying a voltage in the range between 2 and 12 V, and preferably about 3-5 V. For example, when the volume of the brine solution employed in the method of the present invention is between 10 and 20 liters and its density is about 1.3 g/cc, then using electrodes having the dimensions and other characteristics as set forth above, with the current passing through the cell being more than 1 A, results, following electrolysis for about 10-20 minutes, in the brine solution attaining a Redox potential of about 700-1000 mV. A lower current, in the range between 0.2-0.5 Å, is generally effective in producing a brine solution having a Redox potential in the range of 500-700 mV following electrolysis of about 2-5 minutes. Preferred operable Redox working ranges are above 500 mV, preferably between 500 mV and 1000 mV, more specifically between 500 and 900 mV. It should be noted that the effective mixing with the stream of air and the formation of a bubbling liquid as described above also contributes to the development and maintenance of the Redox potential of the brine solution.

It should be noted that in order to achieve a satisfactory sanitization effect in the closed space to be treated, it is not necessary to run the method of the invention under conditions where a brine solution having a redox potential lower than 500 mV is passed through the treatment zone over long time periods (such a brine solution is sometimes named herein as "strong oxidant brine"). In practice, under a routine mode of operation, a brine with a redox potential lower than 500 mV (e.g., between 200-450 mV or even less) may be utilized when running the method of the invention. From time to time, however, the air in the closed space is contacted, under the conditions set forth above, with a brine solution having a redox potential above 500 mV. The treatment may be repeated periodically, for example, once or twice weekly, each time for several hours or up to one or two days. The exact treatment regimen, namely, the length of each treatment interval, in which the method is operated with a brine solution having Redox potential above 500 mV, and the frequency of said treatment, depend on the size of the closed space and the conditions therein (temperature, humidity, the level of contamination in the space), the kind of fungi the inhibition of which is targeted and the characteristics of the column provided in the closed room for effecting the contact between the air and the electrolyzed brine solution having a redox above 500 mV, namely, the working parameters of the apparatus employed for carrying out the method of the invention.

In order to switch from one mode of operation to another, namely, to interrupt the operation of the strong oxidant brine and to allow the rapid regeneration of a brine having Redox potential of less than 500 mV, for example, between 200 and 300 mV, the strong oxidant brine is chemically treated with an effective amount of one or more oxidizer-scavenging compounds. The term 'oxidizer-scavenging compounds' is used herein to indicate organic and inorganic compounds which are useful in removing oxidizers (e.g., oxygen, halogens, oxyhalogens and radicals thereof) from an aqueous solution. Oxidizer-scavenging compounds which act as reducing agents, and specifically, sulfur-based reducing agents, such as water soluble salts of sulfite, bisulfite, thiosulfate, metabisulfite, hydrosulfite or mixtures thereof, as well as other reducing agents such as ascorbic acid, are all within the scope of the present invention. The reducing agent may be fed into the strong oxidant brine in a solid or in a liquid form (e.g., as an aqueous solution). For example, the aforementioned sulfur-containing reducing agents are readily available in the form of aqueous solutions of their sodium salts, preferably with concentration varying in the range between 1 and 30% (w/w), more preferably about 5-10% (w/w). Thus, an aqueous solution of a sulfur-based reducing agent may be fed into the strong oxidant brine, whereby the Redox potential of said brine is decreased and the routinely employed brine, characterized by a Redox potential of less than 500, is restored. For example, when the volume of the strong brine solution employed in the method of the present invention is between 10 and 20 liters, then a solution of sodium bisulfite, or sodium thiosulfate, having a concentration of about 5% (w/v) may be used in order to decrease the Redox potential of the brine. A volume of about 50-200 ml of said bisulfite or thiosulfate solution is generally sufficient for effectively decreasing the Redox potential of sodium chloride brine, calcium chloride brine or Dead Sea brine.

The Redox potential of the brine solution may be also adjusted mechanically, by altering the flow characteristics of the air or of the brine flowing through the treatment zone. Accordingly, the method of the invention further comprises changing the Redox potential of the brine solution between a lower range and a higher range (above 500 mV), said Redox potential being adjusted either electrolytically, mechanically or chemically, wherein the electrolytic adjustment comprises electrolyzing the brine solution, the mechanical adjustment comprises changing the flow characteristics in the treatment zone and the chemical adjustment comprises treating the brine solution with one or more oxidizer-scavenging compounds. The Redox potential of the brine is a readily measurable property, which may therefore serve for monitoring the operation of the method provided by the invention. The measurement of the Redox potential is conveniently achieved by contacting the circulating brine, or a sample of the brine, with a suitable set-up as described above (Pt/Ag/AgCl electrodes). Depending on the results of the Redox potential measured by the set-up set forth above, or an alternative set-up, the Redox potential may be adjusted electrolytically or mechanically (producing the strong oxidant brine) and chemically (for regenerating the routinely employed brine). Thus, the method provided by the present invention may further comprise periodically or continuously measuring the Redox potential of the brine solution, and electrolytically, mechanically or chemically adjusting the Redox potential of the brine based on the measured value of the Redox potential. The set-up which serves for measuring the Redox potential of the brine is positioned at any appropriate location in the pathway of the circulating brine, for example, inside the reservoir holding the brine, or in the feed line used to deliver the brine into the treatment zone. The measured Redox potential may then be used to provide one or more automatic feedback signals to the electrolytic cell in order to adjust its operation, or to a container which holds an aqueous solution of a reducing agent as described above, in order to allow the feeding of said solution into the brine solution and thereby to lessen its Redox potential. Alternatively or in addition, the electrolysis of the brine, for obtaining the strong oxidant brine, and the feeding of a reducing agent into said strong oxidant brine in order to restore the Redox potential to a level below 500 mV, can be adjusted by a human operator based on the observed Redox potential. To this end, the measurement of the Redox potential may be used to generate an alarm signal, to trigger the interference of the human operator once the measurement of the Redox potential indicates a value outside a working range. Alternatively or in addition, the invention may further include periodically or continuously measuring the chlorine level in the closed space, and electrolytically or chemically adjusting the chlorine level based on the measured value. Operable chlorine levels in the treated closed space may vary between 0.1 and 10 ppm, more preferably within 0.1 and 3 ppm. For example, arriving at a chlorine level of about 1 ppm and maintaining the said level for a period of time of about 20-24 hours by the method of the invention has been found to allow an effective sanitization of 25 $m^3$ storage room. Chlorine level of several ppm, namely, up to 10 ppm, may also be practiced under appropriate safety measures. The reduction of the chlorine level in the closed space may be carried out by interrupting the contact of the air with the electrolyzed brine solution, and causing the air to flow through a column and contact with a solution of oxidizer-scavenging compounds, which solution was described above. For this purpose, the air may be either directed to a second, similar column, in which a solution of oxidizer-scavenging compounds is operated, or said solution may be employed in the treatment zone of the invention and circulate therein, in place of the electrolyzed brine solution.

It should be noted that certain brines (e.g., iodide-containing brines), can develop Redox potential greater than 500 mV spontaneously, after having being aerated with the stream of air to be treated under the conditions set forth above, and, furthermore, such brines may maintain their Redox potential over time, though from time to time it may be useful to activate the electrolytic cell for a short duration and to pass said brines through the cell, in order to stabilize their Redox potential within the desired range.

An important feature of the invention is the active layer formed in the treatment zone, in which layer the air and the brine solution mix. As indicated above, the active layer is formed on a substantially horizontally aligned perforated surface, as a result of an upward air flow and downward liquid (brine solution) flow. The term "active layer" indicates a bubbling liquid, namely, a liquid through which a gas (air in the present case) is passed. Perforated surfaces for promoting the formation of a bubbling liquid are generally in the form of meshes or plates with a varying percent open area. The percent of the open area, in the form of perforation, should match the liquid and gas loadings into the treatment zone. The height of the active layer is preferably between 1 and 7 cm (the height depends on the geometrical parameters of the column and the open area of the perforated surface). The air preferably enters the treatment zone at a pressure of not less than 350 Pa, preferably not less than 450 Pa above the ambient atmospheric pressure (although suction mode may also be applied for forcing the air to flow into the treatment zone).

The treated air may carry drops of the brine solution therewith. The method of the invention comprises separating the drops of the brine solution from the treated air, and possibly collecting said drops, and recycling the brine thus recovered for further use.

It has been found that the method of the invention is capable of reducing the microbial load of indoor air in a closed space, and also preventing the development of fungal colonies in solid growth medium (agar dishes) placed in the treated closed space. Notably, agar dishes inoculated with fungi (specifically conidia of *B. cinerea*) and exposed in the treated closed space to air treated by the electrolyzed brine, failed to develop a visible colony even after an incubation period of several days at 25° C. It has been found that treating the air within the closed room with the electrolyzed brine accomplishes the destruction of fungal spores both in the air and solid growth media placed in the closed room. The method of the invention may be used for sanitizing cold storage rooms (e.g., where the temperature is less than 15° C.).

The invention also relates to a novel apparatus for treating air and sanitizing various closed spaces. In its most general form, the apparatus comprises:

a) a gas-liquid contact column, having a perforated surface positioned therein, said perforated surface dividing said column into a first section, which is provided with at least one air inlet opening, and a second section, which is provided with at least one air outlet opening, b) a reservoir for holding a brine solution, connected by means of a feed line into said second section at a point above said perforated surface and below said air outlet opening, and one or more of the following:

c1) an electrolytic cell, comprising electrodes placed in said reservoir or in said feed line;

C2) a drop separator, which may be either physically associated with said column, or provided as a separate unit;

C3) means for forcing a stream of air to flow upwardly in said column, such as air blowing unit, which is preferably connected to the air inlet opening;

C4) a brine solution having the composition specified above, stored within the reservoir.

The apparatus further comprises a measuring electrode and a reference electrode, which electrodes are arranged in said apparatus for measuring the Redox potential of a liquid operating in said apparatus.

More specifically, the apparatus of the invention comprises a gas-liquid contact column having a perforated surface affixed therein, such that said perforated surface divides said column into a first (lower) section, which is provided with at least one air inlet opening, and a second (upper) section, which is provided with at least one air outlet opening. A gas blowing means communicates with said air inlet opening, in order to cause a stream of air to flow into said first section of said gas-liquid contact column and to pass through the perforated surface into the second section of said column. A reservoir (suitable for holding a brine solution) is in fluid communication with the gas-liquid contact column. The apparatus further comprises an electrolytic cell as defined hereinabove. The electrodes of the electrolytic cell are placed in any suitable location within the apparatus. In its most simple configuration, the electrolytic cell comprises two electrodes that are affixed within the reservoir used for holding the brine, or alternatively, within a feed line (e.g., a conduit) used to transfer the brine to the upper section of the column. The apparatus further includes at least a pair of electrodes (a measuring electrode and a reference electrode) connected to a voltmeter, which electrodes are suitably arranged for measuring the Redox (reduction-oxidation) potential of the brine. The apparatus preferably also comprises a chlorine sensor.

More specifically, the apparatus of the invention comprises an elongated, vertically positioned, preferably cylindrical, column. Within the interior space of the column a perforated plate is placed, which plate is perpendicularly arranged relative to the longitudinal axis of said column, and is being affixed to the inner walls of the column, thus dividing the column into lower and upper sections or spaces. An opening is provided in the lateral surface of the lower space of the cylindrical column, which opening serves for air inlet. The upper space of the column comprises an opening which serves as air outlet. A reservoir for holding a brine solution is preferably provided by the lowermost section of the column (where the level of the brine solution is kept below the air inlet opening).

Air blowing unit is preferably connected to the lateral air inlet opening provided in the first section of the column (preferably, but not necessarily, the connection is in a direction tangential to the wall of the column). Suitable air blowing units preferably operate at pressures of not less than 350 Pa (corresponding to about 35 mm H2O), preferably of not less than 470 Pa (corresponding to about 48 mm H20). Air blowing units which can attain the aforementioned pressure values are industrial centrifugal extractor fans, which are commercially available (pressure values reported herein are above the ambient atmospheric pressure).

In operation, the brine solution is continuously driven from the reservoir to the upper section of the column, above the perforated plate, in order to maintain a layer of said brine solution over the upper side of the perforated plate while air streams introduced into the column through the air inlet opening are forced to pass through the perforated plate and contact the brine solution maintained thereon. The air streams which pass through the pores of the perforated plate create a relatively thick layer of a bubbling liquid on top of the perforated plate. As mentioned above, the resulting layer (liquid and bubbles) is referred to herein as "active layer".

Figure 1:
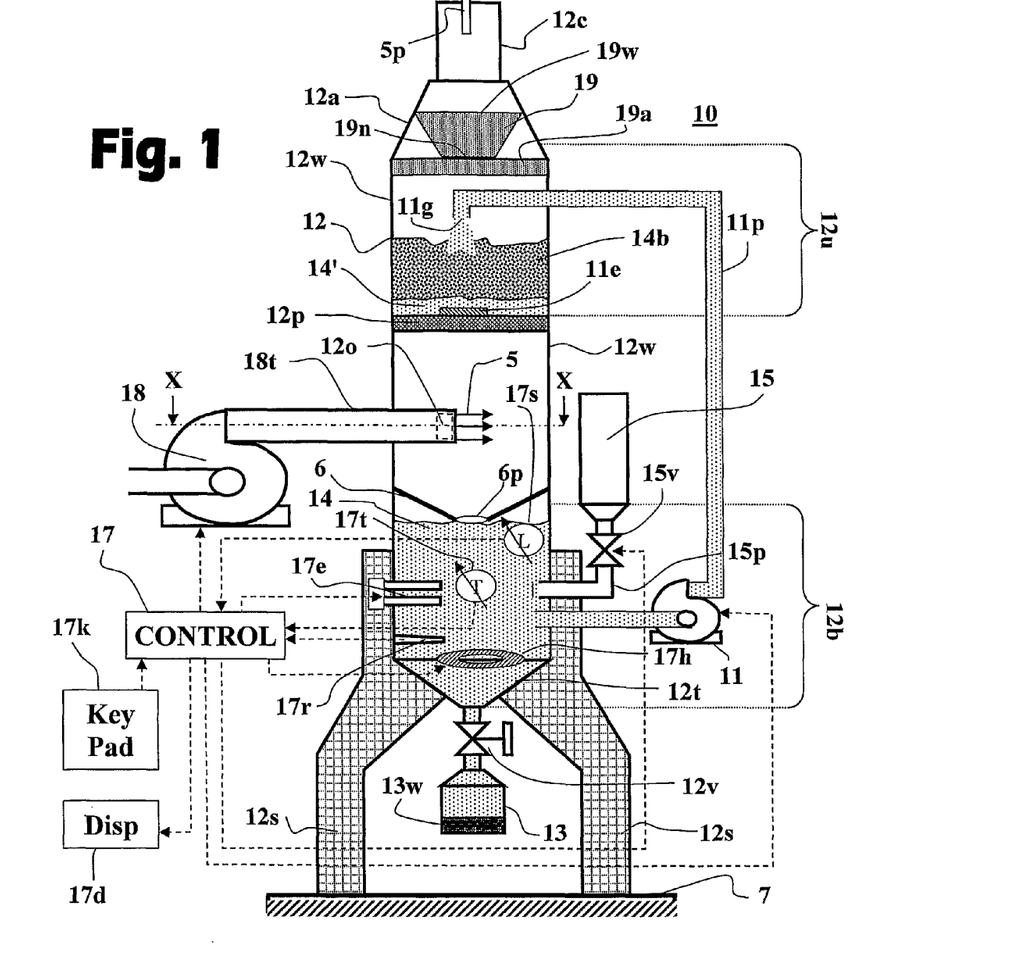
FIG. 1 schematically illustrates a longitudinal-section view of a preferred embodiment of the air treatment apparatus of the invention.

Referring to the drawings, FIG. 1 schematically illustrates a preferred embodiment of the apparatus 10 of the invention comprising a column 12 vertically leveled relative to ground surface 7 by means of lateral supports 12$s$, a perforated plate 12$p$ mounted inside the column 12 in perpendicular to its walls 12$w$, air blower 18 communicating with the air inlet opening 12$o$ formed in the wall 12$w$ of column 12 below perforated plate 12$p$, and a pipe system 11$p$ adapted for piping fluids from the bottom portion 12$b$ of column 12 to its upper portion 12$u$ by means of pump 11 (e.g., magnetic rotary pump).

Column 12, which preferably has a cylindrical shape, is made of chemically resistant material such as, but not limited to, stainless alloys (such as austenitic, ferritic and martensitic stainless steels, titanium alloys, nickel-based super alloys and cobalt alloys) or suitable plastics (such as PVC, CPVC, polyethylene, polypropylene, polybutylene, PVDF, Teflon and polyester). The inner diameter of the column is generally in the range of 30 to 60 cm, preferably about 30 cm, its wall thickness may generally be in the range of 2 to 6 mm, preferably about 3 mm, and its length may range between 0.8 to 2 m, preferably about 1.2-1.5 m. The area of air inlet opening 12$o$ is generally in the range of 100 to 400 cm². In a preferred embodiment of the invention, the opposite sides of the air inlet opening 12$o$ are parallel to one another (e.g. the projection of the opening is rectangular), with a length in the range between 20 and 50 cm, and width in the range between 4 and 8 cm.

Perforated plate 12$p$ is preferably made of a chemically resistant metallic or plastic material, such as those listed above. The thickness of the plate is preferably in the range of 1 to 5 mm. Perforated plate 12$p$ is adapted to tightly fit in column 12 and occupy a cross-sectional area thereof, and is located above air inlet opening 12$o$. The pores in perforated plate 12$p$ preferably occupy 30%-90% of its surface area.

Blower 18 is preferably an electric centrifugal blower capable of providing air streams in the range of 100 to 3000 m³/hr, preferably between 300-1000 m³/hr and more specifically about 800 m³/hr.

The bottom section 12$b$ of column 12 serves for holding the brine solution 14. A treated air outlet 12$c$ is provided in the upper space 12$u$ of column 12. In operation, the brine solution 14 is continuously piped by pump 11 and is delivered to the upper space 12$u$ of column 12, such that a layer of brine solution 14' is maintained above perforated plate 12$p$, while ambient air streams 5 introduced by blower 18 via air inlet opening 12$o$ into column 12 are forced to pass perforated plate 12$p$ and contact the active layer maintained thereon, following which a stream of treated air 5$p$ is passed out of column 12 via air outlet 12$c$.

Partition member 6 is preferably mounted inside column 12 below air inlet opening 12$o$, wherein said partition member 6 has a funnel-like shape, downwardly tapering towards an opening 6$p$. Partition member 6 thus allows brine solution falling from the upper space 12$u$ to be conveniently directed to, and collected in, the lower space 12$b$ of the column.

The outlet of blower 18 preferably communicates with air opening 12$o$ of column 12 via a passage 18$t$ (typically having a rectangular cross-section) adapted to fit over said opening such that the air streams passing therethrough are distributed through the area of air opening 12$o$. The diameter of treated air outlet 12$c$ may generally be in the range of 10 to 30 cm, its cross-sectional area preferably being essentially equal to the area of air opening 12$o$, such that the rate of flow of treated air stream 5$p$ leaving column 12 via air outlet 12$c$ is essentially equal to the rate of flow of ambient air stream introduced into column 12 via air inlet opening 12$o$ (e.g., in the range of 100 to 3000 m³/hr). Alternatively, the diameter of treated air outlet 12$c$ may be the same as the diameter of column 12.

Treated air outlet 12$c$ is preferably connected to a tapering section 12$a$ provided at the upper end of column 12. In order to minimize the escape of liquid drops through the air outlet opening, the drops may be separated from the treated air by passing the air through a porous substrate located within the second section of the column, or by combining a drop separator as a separate unit, for example, a cyclone-type arrangement (which is well known in the art).

For example, one or more drops separating elements may be installed in, or adjacent to, tapering section 12$a$. In one preferred embodiment a frustoconical member 19 made of a porous material (e.g., a sponge), is mounted in tapering section 12$a$ by means of supporting means (not shown), such that its small base 19$n$ is facing perforated plate 12$p$ and its large base 19$w$ is facing treated air outlet 12$c$ and occupies a cross-sectional area of tapering section 12$a$. In this way, the stream of treated air passing via tapering section 12$a$ is forced to pass through conical member 19, thereby separating drops of the brine solution contained therein. Alternatively or additionally, a cross sectional section of column 12 may be also occupied by a piece of porous material 19$a$, preferably adjacent to tapering section 12$a$ for further separating brine drops from the treated air stream passing therethrough.

As indicated above, the drop separator may be provided as a separate unit, to be connected with the air outlet opening 12$c$. One possible arrangement is a cyclone separator, which was mentioned above. Another possible arrangement for a drop separator comprises a conduit connected to the air outlet opening 12$c$, which conduit is downwardly directed, conducting the drops-containing treated air into a suitable tank, where the drops can be collected. The brine thus recovered may be recycled, namely, delivered to the brine reservoir.

The apparatus 10 further comprises an electrolytic cell 17$e$, RedOx electrodes 17$r$ and preferably also level determining means 17$s$, temperature sensing means 17$t$, and a heating element 17$h$, all mounted in the bottom section 12$b$ of the column 12, immersed in brine solution 14, and electrically connected to a control unit 17. The apparatus may further comprise a chlorine sensor (for example, CL2-B1 sensor). Control unit 17 is adapted for monitoring and managing the operation of apparatus 10 responsive to indicating signals received from RedOx electrodes 17$r$, level determining means 17$s$, temperature sensing means 17$t$ and the chlorine sensor. Electrolytic cell 17e is employed for electrolyzing the brine solution passing between its electrodes during operation, preferably, responsive to RedOx readings obtained from RedOx electrodes 17r. Key pad 17k and display unit 17d (e.g., dot matrix or LCD) linked to control unit 17 may be respectively used by control unit 17 for receiving inputs from an operator, and for providing the operator output indications regarding the operation of system 10. Of course, apparatus 10 may comprise additional means connected to control unit 17 for generating visual/vocal output indications (e.g., leds, speakers). Control unit 17 may be implemented by a specially designed control logic circuitry, preferably by a programmable microcontroller. At least one analog to digital converter may be needed for control unit 17 for converting the signals received from RedOx electrode.

In its most simple configuration, an electrolytic cell 17e suitable for use according to the present invention comprises two electrodes that are affixed within the reservoir used for storing the brine. The electrodes are preferably placed in parallel to each other, separated by a gap of 0.3 to 2.0 cm, and more preferably of 0.5 to 1.0 cm. The electrodes are preferably in the form of plates or meshes having a length and a width of about 4 and 10 cm, respectively. Larger or smaller plates and meshes may also be used. The area of the electrodes may preferably vary in the range between 20 to 50 $cm^2$. The electrodes are electrically connected to the opposite poles of a direct electrical current (DC) power supply, which may be activated according to control signals received from control unit 17. The cell typically operates at a current density of $10^3$-$10^5$ Ampere per square meter of anode, applying a voltage in the range between 2 and 12 V, and preferably about 3-5 V. The control unit and the electrodes power supply are preferably adapted to allow control unit to periodically alter the polarity of the electrodes in order to remove electrolytic deposits therefrom.

As mentioned above, a suitable set-up for measuring the Redox potential of the brine solution comprises a measuring electrode made of an inert metal or alloy (a platinum electrode) and a reference electrode (such as Ag/AgCl or calomel). Suitable electrodes are commercially available. The Redox potentials reported herein are measured using Pt/Ag/AgCl electrodes, thus indicating the electrochemical potential which is developed between Pt electrode exposed to the brine and a standard silver-silver chloride electrode.

Figure 2:
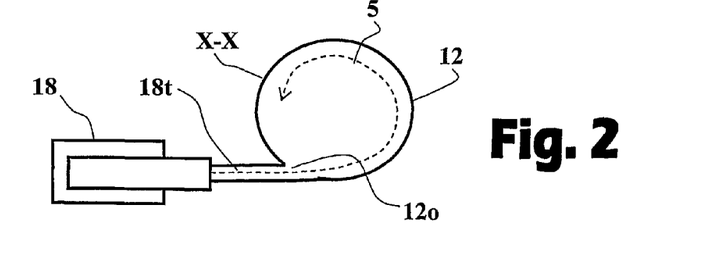
FIG. 2 shows a cross sectional view of the air treatment device of the invention taken along line X-X in FIG. 1A.
Figure 3:
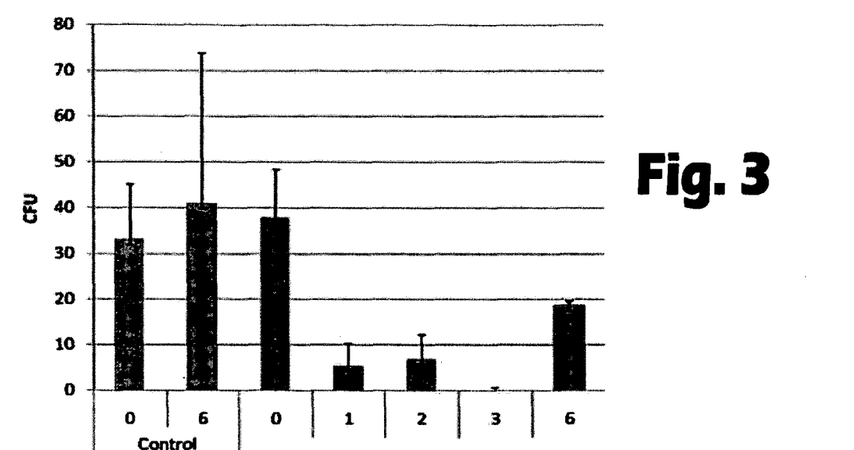
FIG. 3 is a bar graph, representing the amounts of molds in the air treated according to the invention against time.
Figure 4A:
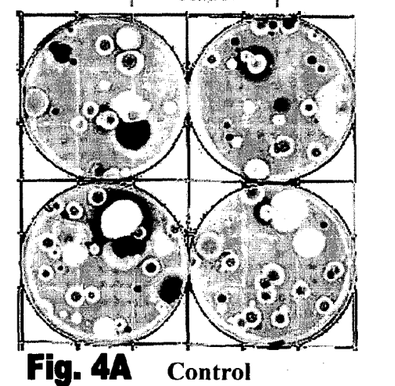
FIG. 4 provides photographs of Petri dishes placed in a control room and a storage room treated with electrolyzed brine according to the invention.
Figure 4B:
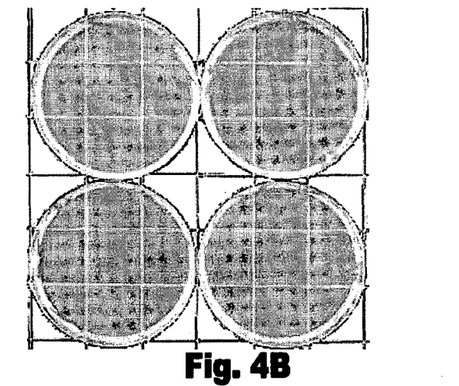
Figure 4C:
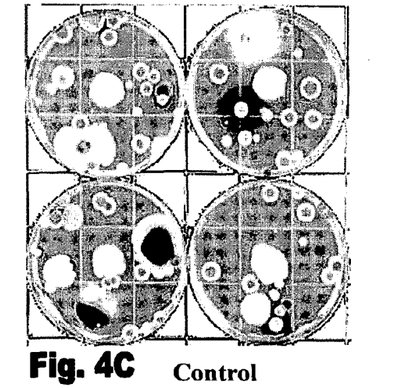
Figure 4D:
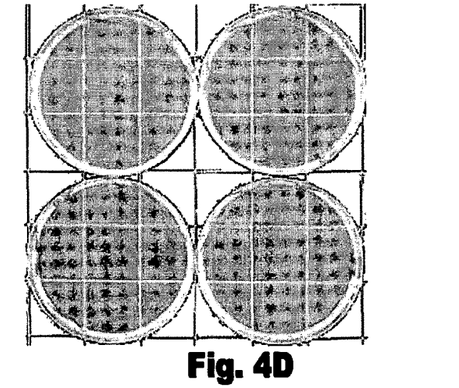

As seen in FIG. 2, showing a cross-sectional view of system 10 taken along line X-X in FIG. 1, blower 18 is attached to the air inlet opening 12o of column 12 such that the ambient air streams 5 introduced thereinto are directed more or less tangentially relative to the wall of column 12.

The bottom end section 12t of column 12 preferably tapers downwardly for draining precipitants formed in brine solution 14. A detachable waist disposal vessel 13 may be attached to bottom end section 12t by means of a short pipe and valve 12v employed for blocking the passage therethrough whenever there is a need to detach waist disposal vessel 13 for removing waist precipitants 13w obtained thereinside. The pipe leading into waist disposal vessel 13 may comprise an optical sensor (e.g., photodiode—not shown) electrically connected to the control unit for providing indications regarding the turbidity of the brine in waist disposal vessel 13, thereby allowing the control unit to produce indications whenever the brine in waist disposal vessel 13 should be replaced.

Pipe 11p communicating with the bottom section 12b of column 12, is preferably introduced into the upper space 12u of column 12, above perforated plate 12p, and its opening is preferably directed downwardly i.e., facing the upper face of perforated plate 12p. Perforated plate may include a relatively small plate 11e (e.g., a metallic disk of about 10 cm in diameter, made of suitable material, e.g., stainless steel) attached to its upper face below the opening of pipe 11g such that the brine solution streamed via pipe 11g encounters plate 11e, in order to prevent downward passage of the streamed brine solution through the pores of perforated plate 12p. It should be noted that the brine solution may be sprayed in the upper portion 12u of column 12 by means of sprinkles (not shown).

According to another preferred embodiment (not shown) of the invention blower 18 is attached to the treated air outlet 12c and in this case it is adapted to apply suction for forcing a stream of ambient air into apparatus 10 through inlet opening 12o, and/or other suitable opening(s) (not shown) provided in apparatus 10.

Signals received by control unit 17 from level determining means 17s provide indications regarding the level of brine solution, and whenever it is determined that the brine level is not within an acceptable range, control unit 17 issues corresponding indications via display unit 17d (and/or vocal or visual indications, if such means are available). Alternatively or additionally, control unit 17 may halt the operation of system 10 whenever it is determined that the brine level is not within an acceptable range. Temperature sensing means 17t and heating element 17h are used by control unit 17 for monitoring and heating the brine solution 14.

In one particular preferred embodiment, apparatus 10 may be employed for controlling the humidity in a closed space by raising the temperature of brine solution 14 and thereby discharging vapor with the stream of treated air 5p leaving system 10 via treated air outlet 12c. Alternatively or additionally, whenever the signals received by control unit 17 from level determining means 17s indicate that apparatus 10 absorbed fluids from the ambient air streamed therethrough it may activate heating element 17h until the level of brine solution in column 12 is restored back into the acceptable range of brine solution levels.

Various aspects of operation of apparatus 10 may be managed by control unit 17 according to readings received from RedOx electrodes 17r, in particular, the monitoring and managing of the activity of brine solution 14 by means of electrolytic cell 17e, as discussed hereinabove.

Apparatus 10 further comprises a container 15, for holding a solution of oxidizer-scavenging compounds, as described hereinabove, wherein said container communicates with the bottom portion 12b of column 12 through a pipe 15p. Valve 15v, which is provided on pipe 15p, may be used for controlling the feeding of the solution of the oxidizer-scavenging compounds into the brine, in order to reduce the Redox potential of the brine, if desired. Preferably, valve 15v is a controllable valve electrically connected to control unit 17. In this way control unit 17 may be adapted to provide valve 15v control signals for altering its state and thereby controlling the passage of the solution of the oxidizer-scavenging compounds through pipe 15p into the bottom portion 12b of column 12, in order to decrease the Redox potential of the brine.

By way of example, a volume of 15 to 20 liters of brine solution is contained in column 12. In normal operation of apparatus 10, control unit 17 activates electrolytic cell 17e for electrolyzing the brine, adjusting the Redox potential of the brine to a certain value, as measured by RedOx electrodes 17r. If the Redox potential exceeds a desired, predetermined level, then corresponding control signals may be delivered for opening valve 15v in order to introduce a volume of the solution of the oxidizer-scavenging compounds into bottom portion 12b of column 12.

Blower 18 is preferably a type of controllable centrifugal blower (e.g., having PWA or voltage control) capable of receiving control signals from control unit and adjusting its operation accordingly. Advantageously, control unit 17 may be adapted for producing control signals for altering the rates of ambient air flow produced by the blower 18, responsive to readings received from the RedOx electrode 17*r*. It has been observed that some brine solutions respond to enhanced aeration conditions by a rapid increase of their redox potential. In this way, the Redox potential of the brine solution may be controlled by control unit 17, for example, by increasing the velocity of the ambient air stream.

Apparatus 10 may be adapted to operate in two main modes of operations: i) the routine air treatment mode, wherein the Redox potential of the brine solution is less than 500 mV, as described hereinabove; and ii) sanitization mode, in which the electrolytic cell 17*e* is operated to produce brines having high Redox potentials (e.g., 700-1000 millivolts), whereby oxyhalogens and other oxidant species are produced and released in significant amounts into the space to be treated by the stream of treated air leaving column 12 via air outlet 12*c*. This mode of operation is particularly useful for rapidly sanitizing various spaces (e.g., rooms, infected facilities, hospital compartments). The operation mode of apparatus 10 may be changed back from the sanitization mode into the routine treatment mode by feeding suitable quantities of a solution of reducing agents kept in container 15 into brine solution 14, such that the measurements carried out by the RedOx electrodes 17*r* indicate that the Redox potential of the brine has been restored to the routine range (about 200-400 mV).

EXAMPLES

Example 1

Reducing the Load of Microbial Contamination in the Air of a Storage Room and Preventing the Development of Fungus Colonies on Artificial Media The apparatus shown in FIG. 1 was placed in a 25 $m^3$ storage room, operating at a temperature of 11.5° C. and relative humidity of 93.3%. The control storage room had a similar volume and operated at a temperature of 8.9° C. and relative humidity of 94.4%. The apparatus was operated continuously for 96 hours, using about 15 liters of aqueous solution of sodium chloride having concentration of about 30% by weight. The electrolytic cell operated under the following parameters: current—4 Ampere, voltage—5 volt. The Redox potential of the brine was adjusted to about 850 mV during the treatment period. The air was introduced into the apparatus by the blower at a rate of 300 $m^3$/hour. The blower operated at its maximal pressure, about 470 Pa (Operable working pressures according to the invention are preferably between 350 Pa and 750 Pa).

The air was sampled to determine the effect of the treatment on the presence of molds in the cold storage rooms. Sampling was performed with Biotest RCS Air Sampler set for 200 liters and equipped with strips of media for detection of molds and yeasts (Hy lab, Israel). Sampling was performed via a custom adaptor mounted through the wall of both cold storage rooms. Thus, the air was sampled without entering the cold storage rooms. The Sampling was performed before initiating the operation of the apparatus and after 24, 48, 72, and 144 h, in triplicates (the last sampling was carried out 48 hours after turning off the apparatus). The results of the measurements are presented in FIG. 3.

FIG. 3 is a bar graph in which the abscissa indicates the times (in days) at which the air in the storage and control rooms was sampled, and the ordinate indicates the amounts of molds in the air. The two left bars correspond to the measurements carried out in the control room, indicating high level of microbial load prior to the commencement of the experiment (day 0), and also six days after the start of the experiment. As to the measurements reported for the storage room treated according to the invention, it is noted that a significant reduction in the level of air contamination is achieved already 24 hours after the start of the experiments (day 1). As indicated above, the apparatus was operated for 4 days; after 72 hours (day 3), the level of contamination reduced to about zero. Two days following the interruption of the operation of the apparatus, the level of air contamination increased (day 6), but was still lesser than the initial level measured on day 0.

In addition to the air sampling described above, petri dishes that contained Potato Dextrose Agar (PDA) were exposed in both cold storage rooms for 24 or 48 h. Half of the plates were also inoculated with a drop of 10 μl that contained $10^4$ conidia of *B. cinerea*. After exposure, the petri dishes were closed and incubated for 5 days at 25° C. Agar dish exposure consisted of five replicates.

FIG. 4 provides photographs of the Petri dishes placed in the control room and the storage room treated according to the invention (the left and right columns, respectively). The development of visible colonies (of the fungus *B. cinerea* and apparently of other fungi) is clearly illustrated in all agar dishes that were placed in the control room (FIG. 4*a* relates to the non-inoculated PDA plates, whereas FIG. 4*c* relates to the inoculated PDA plates).

In contrast, no bacterial colonies were observed in the agar dishes placed in the storage room that was treated according to the invention. (FIG. 4*b* relates to the non-inoculated PDA plates, whereas FIG. 4*d* relates to the inoculated PDA plates). It should be pointed out that under normal circumstances, exposure of agar dishes for 15 min in a contaminated room is sufficient to infest the dishes completely. Furthermore, Conidia of *B. cinerea* that were placed in the center of the agar dish for 24 h, failed to develop visible colonies even after one week of incubation, suggesting that they were actively killed following the treatment of the invention.

Example 2

Destroying Fungal Colonies by Air Treated with an Electrolyzed Brine

A further experiment was carried out in order to illustrate that exposure of conidia of *Botrytis* to air treated by the electrolyzed brine according to the invention results in an essentially complete killing of said conidia.

The apparatus described in FIG. 1 was operated in a cold storage at a temperature of 9.68±0.35° C. and relative humidity of 92.9±0.8 under the conditions described in Example 1. In the control storage room used for the purpose of comparison, the temperature was 9.66±0.19° C. and the relative humidity was 96.1±1.9.

The following three sets of PDA plates were prepared:
Set 1: Conidia after germination—$10^4$ conidia were placed on a center of a PDA plate. The plates were incubated for 24 h at 25° C. Then, the plates were exposed to the air treated with the electrolyzed brine for specified periods of time as described below.
Set 2: Freshly harvested conidia of Botrytis were placed on PDA plates and were immediately subjected to the air treated with the electrolyzed brine for specified periods of time as described below.
Set 3: control PDA plates without conidia.

The plates (of all sets) were exposed to air treated by the electrolyzed brine in the cold storage room for the following periods of times: 0 (control), 1, 3, 6, 12, and 24 h. Subsequently, the plates were closed and transferred to the control room and after 24 h all the plates were incubated at 25° C. for 4 days. The development of the colonies was documented by radial growth measurement and by photography. The experiment was carried out in 5 replications.

Figure 5:
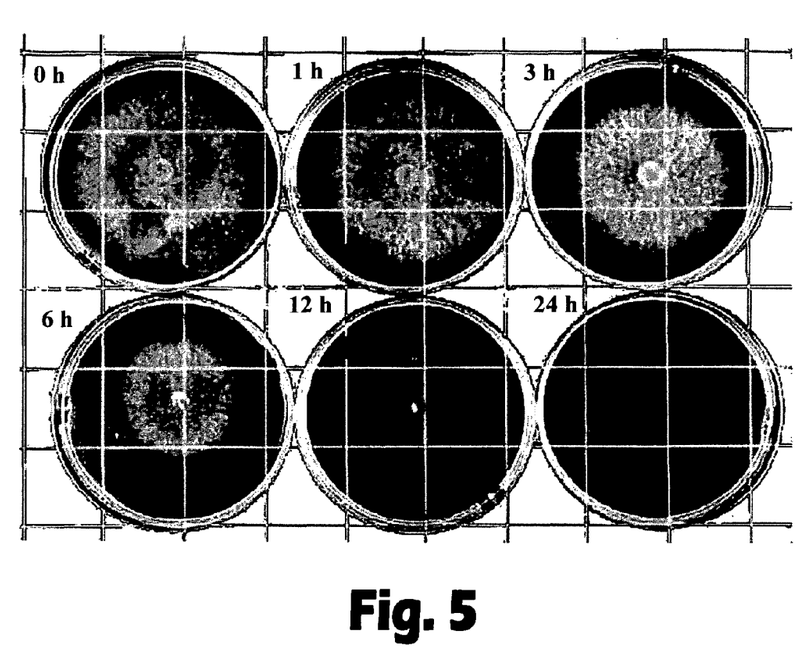
FIG. 5 provides photos of Petri plates exposed to air treated with the electrolyzed brine according to the invention.
Figure 6:
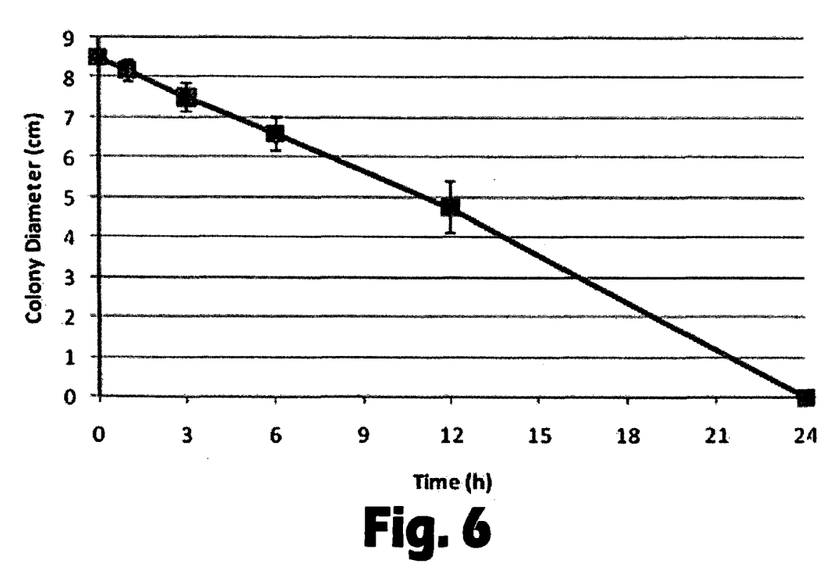
FIG. 6 is a graph showing the diameter of the colonies formed in Petri dishes exposed to air treated with electrolyzed brine according to the invention, as a function of exposure time of the plate to said air.

Regarding the second set, the results are illustrated in FIGS. 5 and 6. FIG. 5 provides photos of the PDA plates (the photos were taken six days after the start of the experiment; the time of exposure (in hours) of each plate to the treated air prior to the incubation is indicated next to each plate). It is apparent that exposure of the conidia to the air treated with the electrolyzed brine for 24 h results in a complete killing of the conidia, as they failed to grow and develop a colony after 7 d of incubation at 25° C. The correlation between the duration of exposure of the PDA plates to the air treated with the electrolyzed brine, and the degree of colony developed in the PDA plate is illustrated by the graph shown in FIG. 6, where the diameter of the colony formed in plotted against the duration of exposure of the plate to the treated air.

Figure 7:
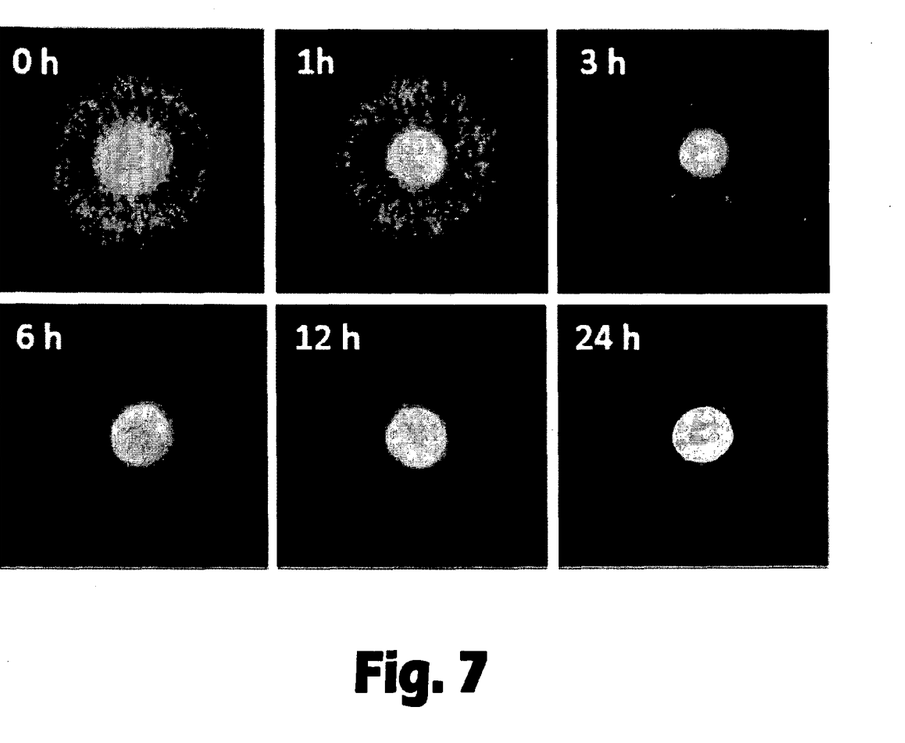
FIG. 7 shows photos of Petri dishes exposed to air treated with electrolyzed brine according to the invention.

Regarding the first set, in which conidia were germinated on the PDA plates at 25° C. for 24 h before being subjected to the treatment, the results are illustrated in FIG. 7, where photos were taken three days after the exposure of the plates to the air treated with the electrolyzed brine. The efficacy of the 24 h duration exposure time is clearly apparent: no radial growth of the colony is observed, though hyphae developed on the spot of inoculation.

Example 3

The following experiment was carried out in order to illustrate the role of the active layer in the sanitization of a closed space.

The experiment was carried out in two cold storage room. The temperature and the level of humidity in the two storage rooms were essentially the same (around 11-12.5° C. and 80-90% humidity). In the first room (room 1), the apparatus of the invention was allowed to operate under conditions whereby an electrolyzed brine is circulated and a bubbling liquid is formed, whereas the second room (room 2) served as a control (the air passes through the apparatus without circulation of the electrolyzed brine). The conditions of the electrolysis were the same in both rooms (the electrolytic cells operated with a current of 4.1 A and voltage of 3.6 V). It should be noted that the initial level of contamination measured in room 1 prior to the initiation of the experiment was higher than that measured for the control room.

In each room, two positions having different heights above the floor were arranged (25 cm or 120 cm above the floor, indicated L or H, respectively).

PDA petri plates were prepared. Half of the plates were inoculated with conidia of B. cinerea, as described above. The PDA plates (72 in total) were then divided into nine equal groups (designated herein G1, G2, . . . G9), each group consisting of four non-inoculated and four inoculated PDA plates. Each group is further divided into two identical subsets, each subset consisting of two inoculated and two non-inoculated plates.

The groups of plates G1, G2 . . . G9 were placed in the two rooms starting at different times, and/or for different exposure times, with the eight members of each groups being divided as follows: in each room (1 and 2), a pair consisting of an inoculated plate and a non-inoculated plate (designated I and N, respectively), was placed on each of the two available positions (L and H). Following a prescribed period of time, the eight plates belonging to a given group were transferred to an incubation for 72 hours at 25° C., following which each plate was tested in order to determine for the number of colonies which were developed therein.

The table below summarizes the arrangement described above, indicating the time at which each group of plates was placed in the rooms, the period of treatment, during which the group was exposed to the operation of the apparatus, and reports, for each plate, the number of visible colonies.

| Group | Start (time) | Exposure (hours) | Room 1 Active layer | | | | | Room 2 No active layer | | | | |
| --- | --- | --- | --- | --- | --- | --- | --- | --- | --- | --- | --- | --- |
| | | | LN | LI | HN | HI | mean | LN | LI | HN | HI | mean |
| G1 | 0 | 3 | 17 | 15 | 20 | 15 | 16.8 | 32 | 34 | 46 | 22 | 33.5 |
| G2 | 0 | 6 | 12 | 3 | 8 | 4 | 6.75 | 63 | 38 | 64 | 46 | 52.75 |
| G3 | 0 | 9 | 5 | 3 | 4 | 2 | 3.5 | 68 | 47 | 67 | 42 | 56 |
| G4 | 0 | 12 | 0 | 4 | 4 | 1 | 2.25 | 83 | 45 | 90 | 42 | 65 |
| G5 | 0 | 24 | 0 | 0 | 0 | 0 | 0 | 102 | 32 | 75 | 33 | 60.5 |
| G6 | 3 | 3 | 3 | 1 | 3 | 4 | 2.75 | 35 | 15 | 29 | 16 | 23.75 |
| G7 | 3 | 9 | 1 | 1 | 0 | 2 | 1 | 55 | 33 | 52 | 23 | 40.75 |
| G8 | 6 | 3 | 0 | 2 | 0 | 0 | 0.5 | 25 | 9 | 34 | 6 | 18.75 |
| G9 | 6 | 6 | 0 | 0 | 0 | 0 | 0 | 43 | 6 | 15 | 28 | 23 |

LN: low position, non-inoculated plate
LI: low position, inoculated plate
HN: High position, non-inoculated plate
HN: High position, inoculated plate The results reported in the table above indicate that exposure of conidia of *Botrytis* to air, which was allowed to mix with a brine having redox potential above 500 mV (between 700-900 mV) under conditions where a bubbling liquid was formed, results in an essentially complete killing of said conidia. Inferior results (in terms of increased colony development) were observed in the case where no bubbling liquid was formed.

The invention claimed is:

1. A method for reducing the biological contamination of indoor air and sanitizing the walls and surfaces in a closed space, which method comprises causing a stream of air to flow upwardly through a treatment zone, and to contact, on a substantially horizontally aligned perforated surface, with a stream of brine solution having Redox potential of not less than 500 mV, whereby an active layer is formed on said horizontally aligned perforated surface, in which layer the brine and air mix, and delivering the treated air which exits said treatment zone into the space to be sanitized, wherein the method further comprises separating drops of said brine solution from said treated air and periodically or continuously measuring the chlorine level in said closed space.

2. A method according to claim 1, wherein the treatment zone is provided by a vertically positioned column, in which the stream of brine solution flows downwardly.

3. The method according to claim 1, wherein the brine solution having a Redox potential above 500 mV is generated by means of electrolysis in an electrolytic cell.

4. The method according to claim 1, which further comprises occasionally changing the Redox potential of the brine solution between the ranges below and above 500 mV, wherein said Redox potential is adjusted electrolytically, mechanically or chemically, wherein the electrolytic adjustment comprises electrolyzing the brine, the mechanical adjustment comprises changing the flow characteristics within the treatment zone and the chemical adjustment comprises treating the brine with an oxidizer-scavenging compound.

5. A method according to claim 4, wherein the oxidizer-scavenging compounds include a sulfur-containing agent selected from the group consisting of sulfite, bisulfite, thiosulfate, metabisulfite, hydrosulfite compounds or mixtures thereof.

6. A method according to claim 1, which further comprises periodically or continuously measuring the Redox potential of the brine solution, and electrolytically, mechanically or chemically adjusting the Redox potential of the brine based on the measured value of the Redox potential.

7. A method according to claim 1, wherein the brine solution has a salt concentration of not less than 10% (w/w), said brine solution containing one or more water soluble salts represented by the formulas $MX$, $M_2X$ and $MX_2$, wherein X is selected from the group consisting of chloride, bromide, iodide, sulfate and nitrate anions, and M indicates a metal cation selected from the group consisting of lithium, sodium, potassium, calcium, magnesium and zinc, and mixtures thereof.

* * * * *